(12) United States Patent  
Brisken

(10) Patent No.: US 6,503,243 B1
(45) Date of Patent: *Jan. 7, 2003

(54) METHODS AND SYSTEMS FOR THE INHIBITION OF VASCULAR HYPERPLASIA

(75) Inventor: Axel F. Brisken, Fremont, CA (US)

(73) Assignee: Pharmasonics, Inc., Sunnyvale, CA (US)

( * ) Notice: Subject to any disclaimer, the term of this patent is extended or adjusted under 35 U.S.C. 154(b) by 140 days.

This patent is subject to a terminal disclaimer.

(21) Appl. No.: 09/653,033

(22) Filed: Sep. 1, 2000

Related U.S. Application Data

(63) Continuation of application No. 09/223,230, filed on Dec. 30, 1998, now Pat. No. 6,210,393.
(60) Provisional application No. 60/070,236, filed on Dec. 31, 1997.

(51) Int. Cl.[7] .............................................. A61M 31/00
(52) U.S. Cl. ......................... 604/508; 604/22; 128/898
(58) Field of Search ............................ 604/22, 65, 67, 604/35, 104, 158, 164, 508, 509, 500, 510, 513; 606/108, 198; 623/1.11, 1.15, 1.42; 600/1, 3, 467, 471; 128/878

(56) References Cited

U.S. PATENT DOCUMENTS

| | | | |
|---|---|---|---|
| 5,059,166 A | 10/1991 | Fischell et al. | |
| 5,163,421 A | 11/1992 | Bernstein et al. | |
| 5,199,939 A | 4/1993 | Dake et al. | |
| 5,213,561 A | 5/1993 | Weinstein et al. | |
| 5,269,291 A | 12/1993 | Carter | |
| 5,302,168 A | 4/1994 | Hess | |
| 5,312,430 A | 5/1994 | Rosenbluth et al. | |
| 5,315,998 A | 5/1994 | Tachibana et al. | |
| 5,318,014 A | 6/1994 | Carter | |
| 5,344,395 A | 9/1994 | Whalen et al. | |
| 5,362,309 A | 11/1994 | Carter | |
| 5,474,531 A | 12/1995 | Carter | |
| 5,514,086 A | 5/1996 | Parisi et al. | |
| 5,527,337 A | 6/1996 | Stack et al. | |
| 5,599,294 A | 2/1997 | Edwards et al. | |
| 5,599,844 A | 2/1997 | Grainger et al. | |
| 5,616,114 A | 4/1997 | Thortonton et al. | |
| 5,836,896 A | 11/1998 | Rosenchein | |
| 5,840,031 A | 11/1998 | Crowley | |
| 5,846,218 A | 12/1998 | Brisken et al. | |
| 6,210,393 B1 * | 4/2001 | Brisken ........................ 604/22 |

FOREIGN PATENT DOCUMENTS

WO      WO 98/48711      11/1998

OTHER PUBLICATIONS

Alter et al., "Ultrasound inhibits the adhesion and migration of smooth muscle cells in vitro" Ultrasound in Medicine (1998) 24(5):711–721.

Bendeck et al., "Inhibition of matrix metalloproteinase activity inhibits smooth muscle cell migration but not, neointimal thickening after arterial injury" (1996) Circ. Res. 78:38–43.

He et al., "Application of ultrasound energy for intracardiac ablation of arrhythmias" Eur. Heart J. (1995) 16:961–966.

(List continued on next page.)

Primary Examiner—Anhtuan T. Nguyen
(74) Attorney, Agent, or Firm—Townsend and Townsend and Crew LLP

(57) ABSTRACT

Post-interventional neointimal hyperplasia in arteries is treated by the application of ultrasonic energy. Usually, an intravascular catheter having an interface surface is positioned at a target site in the artery which has previously been treated. The interface surface is vibrationally excited to apply energy to the arterial wall in a manner which inhibits smooth muscle cell proliferation in the neointimal layer.

23 Claims, 13 Drawing Sheets

OTHER PUBLICATIONS

Rosenchein et al., "Experimental ultrasonic angioplasty: Disruption of atherosclerotic plaques and thrombi in vitro and arterial recanalization in vitro" JACC (1990) 15:711–717.

Kaufman et al., "Lysis and viability of cultured mammalian cells exposed to 1MHz ultrasound" Ultrasound Med. Biol. (1977) 3:21–25.

Schwartz et al., "Vascular cell proliferation dynamics: Implications for gene transfer and restenosis" Gene Translation in the Cardiovascular System: Experimental Approaches and Therapeutic Implications (1997) Keith L. Marsh, Editor, Kluwer Academic Publications, Netherlands, pp. 293–305.

Siegel et al., "Unltrasound angioplasty" J. Invasive Cardiol. (1991) 3:135.

* cited by examiner

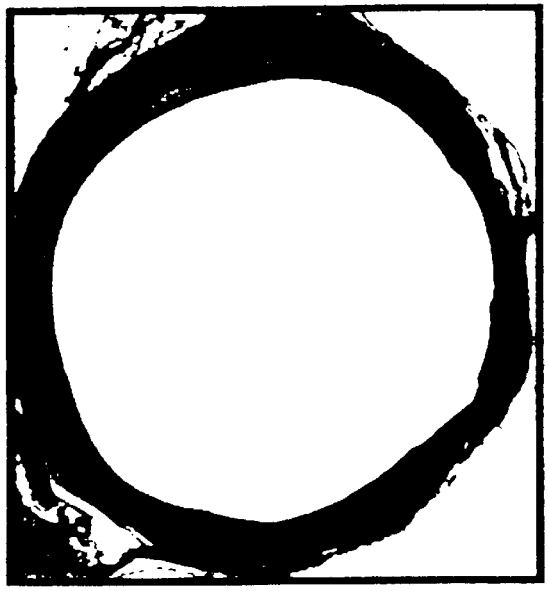 
FIG. 10A  FIG. 10B
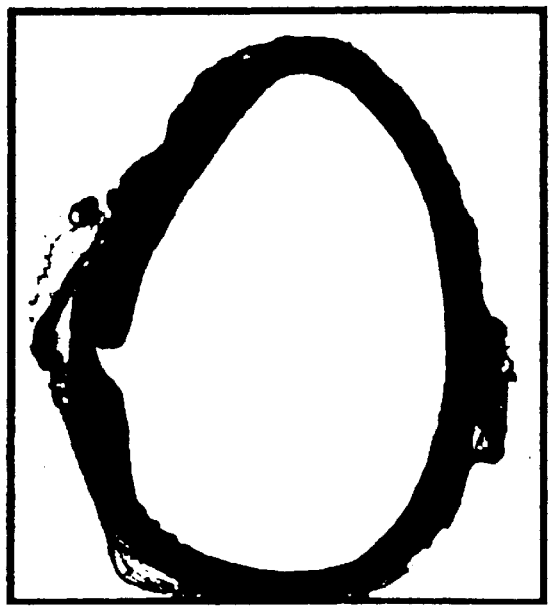 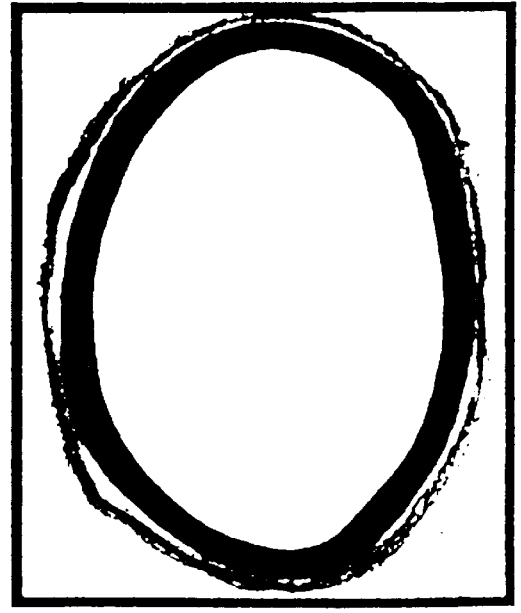
FIG. 11A  FIG. 11B

 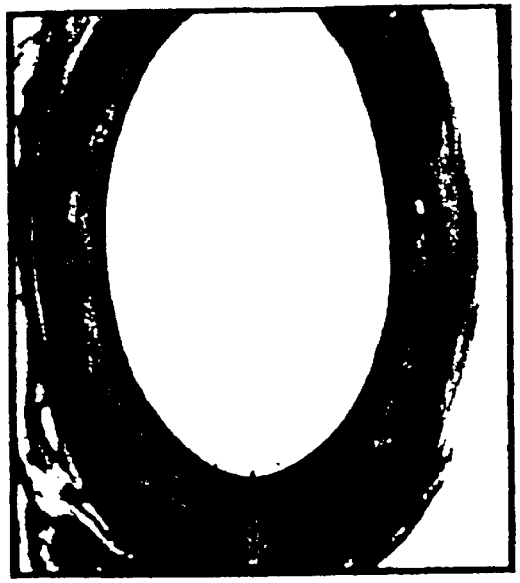
*FIG. 12A*        *FIG. 12B*
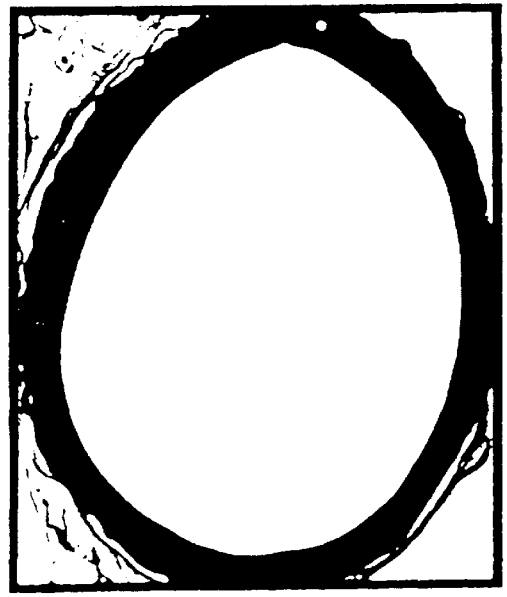 
*FIG. 13A*        *FIG. 13B*

METHODS AND SYSTEMS FOR THE INHIBITION OF VASCULAR HYPERPLASIA

CROSS-REFERENCES TO RELATED APPLICATIONS

This application is a continuation of application Ser. No. 09/223,230, filed on Dec. 30, 1998, now U.S. Pat. No. 6,210,393, which claimed the benefit of provisional application No. 60/070,236, filed on Dec. 31, 1997, the full disclosures of which are incorporated herein by reference.

BACKGROUND OF THE INVENTION

1. Field of the Invention

The present invention relates generally to medical devices and methods. More particularly, the present invention relates to methods and apparatus for inhibiting neointimal hyperplasia in arteries following angioplasty, stenting, or other intravascular procedures for treating atherosclerotic disease.

A number of percutaneous intravascular procedures have been developed for treating atherosclerotic disease in a patient's vasculature. The most successful of these treatments is percutaneous transluminal angioplasty (PTA) which employs a catheter having an expansible distal end, usually in the form of an inflatable balloon, to dilate a stenotic region in the vasculature to restore adequate blood flow beyond the stenosis. Other procedures for opening stenotic regions include directional atherectomy, rotational atherectomy, laser angioplasty, stents and the like. While these procedures, particularly PTA followed by stenting, have gained wide acceptance, they continue to suffer from the subsequent occurrence of restenosis.

Restenosis refers to the re-narrowing of an artery within weeks or months following an initially successful angioplasty or other primary treatment. Restenosis afflicts up to 50% of all angioplasty patients and results at least in part from vascular smooth muscle cell proliferation in response to the injury caused by the primary treatment, generally referred to as "neointimal hyperplasia." Blood vessels in which significant restenosis occurs will require further treatment.

A number of strategies have been proposed to reduce restenosis. Stich strategies include prolonged balloon inflation, treatment of the blood vessel with a heated balloon, treatment of the blood vessel with ionizing radiation, the administration of anti-thrombotic drugs following the primary treatment, stenting of the region following the primary treatment, and the like. While enjoying different levels of success, no one of these procedures has proven to be entirely successful in treating all occurrences of restenosis.

Of particular interest to the present invention, the application of ionizing radiation from radioisotopes following angioplasty has shown great promise for the inhibition of hyperplasia. Despite its great promise, the use of intravascular radiation suffers from a number of proven and suspected deficiencies. Such ionizing radiation treatments do not appear to promote healing of the endothelial layer which forms over the neointimal layer, particularly over stented regions of a treated artery. The radiation may also be harmful to the medial region of the arterial wall, subjecting the patient to long-term risk. On a practical level, the need to handle and dispose of radioisotopes is problematic and presents some risk to both the patient and the individuals treating the patient. While the use of isotopes having a very short half-life reduces these problems somewhat, the fabrication and inventory maintenance of catheters and devices employing such isotopes is difficult because the very short shelf-life. It will be appreciated that the window of opportunity for using isotopes having a very short half-life is quite limited.

The use of ultrasound energy for treating restenosis on a blood vessel has been proposed in U.S. Pat. No. 5,836,896. In particular, that patent teaches that high amounts of ultrasonic energy can be delivered to a blood vessel in order to reduce the viability, migration, and adhesion of smooth muscle cells. The ultrasonic energy is delivered under conditions which cause cavitation within the smooth muscle cells. The preferred operational parameters are low frequency (15 kHz to 250 kHz) and high energy capable of causing the intended cavitation. In a particular example, use of a longitudinal vibration transmission wire to first recanatize an artery and subsequently radiate the vascular intima to inhibit smooth muscle cell migration, viability, and adherence is described. While positive results are reported, there are no controls to confirm whether the post-recanalization therapy was responsible for the observed patency.

For these reasons, it would be desirable to provide alternative methods and apparatus for the treatment of intimal hyperplasia in arteries following angioplasty, stenting, and other recanalization treatments. It would be particularly desirable to provide methods and apparatus for the application of vibrational energy to the arterial wall, where the energy would at least partly inhibit excessive cell proliferation of vascular smooth muscle cells in the neointimal layer which forms following a primary treatment and which can result in hyperplasia and subsequent restenosis of the blood vessel. It would be even more desirable if the energy source were generated in situ within the blood vessel and were of a type which may be readily turned on and turned off without exposing the patient and treating personnel to significant risk. The apparatus intended for performing the method should be suitable for vascular introduction, preferably via percutaneous intravascular access. In addition, it would be desirable to provide methods for inhibiting the hyperproliferation of vascular smooth muscle cells in the neointimal layer following arterial injury without substantially diminishing the viability or migration capability of the cells. It would be still further desirable to provide for ultrasonic and other vibrational therapy for the inhibition of neointimal hyperplasia without inducing substantial cavitation or creating substantial heating in the arterial wall being treated. Such treatments would desirably promote healing and re-endothelialization of the arterial wall. At least some of these objectives will be met by the invention described hereinafter.

2. Description of the Background Art

Intravascular inhibition of hyperplasia by exposure to radioisotopes is described in a number of patents and publications, including U.S. Pat. Nos. 5,616,114; 5,302,168; 5,199,939; and 5,059,166. The therapeutic application of ultrasonic energy is described in a number of patents and publications including U.S. Pat. Nos. 5,362,309; 5,318,014; 5,315,998, WO 98/48711; and others.

The application of intravascular ultrasound for inhibiting restenosis by decreasing the migration, viability, and adhesion of vascular smooth muscle cells via a cavitation mechanism is suggested in U.S. Pat. No. 5,836,896. Vascular smooth muscle cell migration, however, has been shown not to contribute significantly to neointimal thickening after arterial injury. See, Bendeck et al. (1996) *Circ. Res.* 78:38–43. Vascular smooth muscle cell proliferation, migration, and adhesion have been shown to decrease in cell culture in response to ultrasonically induced cavitation. Alter et al. (1998) 24:711–721. See also Rosenchein et al. (1990) *JACC* 15:711–717 and Siegel et al. (1991) *J. Invasive Cardiol.* 3:135 which describe thrombolysis via the cavitation mechanism.

A high frequency ultrasonic catheter intended for tissue ablation which employs an air-backed transducer is described in He et al. (1995) Eur. Heart J. 16:961–966. Cell lysis of mammalian cell lines maintained in vitro is described in Kaufman et al. (1977) Ultrasound Med. Biol. 3:21–25. Catheters suitable for performing at least some methods according to the present invention are described in co-pending application Ser. Nos. 08/565,575; 08/566,740; 08/566,739; 08/708,589; 08/867,007, and 09/223,225, and assigned to the assignee of the present invention, the full disclosures of which are incorporated herein by reference.

SUMMARY OF THE INVENTION

The present invention provides for treatment of a target site within a coronary artery or other blood vessel subject to occlusion from neointimal hyperplasia. By "neointimal hyperplasia," it is meant that excessive cell proliferation occurs at the target site within the blood vessel, usually resulting from treatment of a primary occlusion by angioplasty, atherectomy, stenting, or other conventional intravascular treatment for widening or de-bulking the primary occlusion. It has been found that such primary treatments often damage the cells lining the blood vessel in a manner which results in an injury response characterized by secretion of extracellular matrix and excessive proliferation of the smooth muscle cells lining the blood vessel which together make up the neointimal layer lining the arterial wall.

Treatment according to the present invention is effected by exposing a target site within the arteries at risk of hyperplasia to vibrational energy at a mechanical index and for a time sufficient to inhibit hyperplasia of smooth muscle cells within the neointimal layer of the arterial wall. Surprisingly, it has been found that the strength of vibrational energy (as measured by the mechanical index) and the duration of the treatment (as measured by elapsed treatment time, duty cycle, and pulse repetition frequency (PRF)) can be selected to provide highly effective hyperplasia inhibition in the neointimal layer without significant damage to surrounding tissues or structures within the artery. In particular, by exposing an arterial target site at risk of neointimal hyperplasia to a vibrational energy having a mechanical index in the range from 0.1 to 50, preferably from 0.2 to 10, and more preferably from 0.5 to 5, for a treatment time in the range from 10 seconds to 1000 seconds, preferably from 30 seconds to 500 seconds, and more preferably from 60 seconds to 300 seconds, the proliferation of vascular smooth muscle cells in the neointimal layer of the artery can be reduced by at least 2% (in comparison with untreated controls) after seven days, often at least 4%, and sometimes 6% or greater. The resulting reduction in hyperplasia mass after 28 days will typically be at least 10%, usually at least 20%, and preferably at least 30%. Such inhibitions can be achieved without significant necrosis of the smooth muscle cells. Prior methods of hyperplasia inhibition which rely on necrosis present a substantial risk of injuring not only the neointimal layer (which can prevent rapid and/or normal healing of the layer) but also the medial layer and other arterial tissues and structures. The methods of the present invention will preferably be performed under conditions which cause little or no cavitation within the smooth muscle cells and other cells within or near the treatment region. While the initiation of cavitation will be governed to a large extent by the power and mechanical index off the vibrational energy, the presence of cavitation nucleii, such as gas microbubbles, can also contribute to cavitation. Thus, the methods of the present invention will preferable be performed in the absence of introduced microbubbles and/or other cavitation nucleii. Moreover, the treatment conditions of the present invention will result in little or no inhibition of migration of smooth muscle cells into the neointimal layer. Instead, the migration will be generally normal, but the migrated cells will have a quiescent phenotype rather than the proliferative phenotype associated with the formation of neointimal hyperplasia. In their proliferative phenotype, vascular smooth muscle cells not only divide rapidly but also excrete extracellular matrix which accounts for most of the volume of the neointimal layer responsible for hyperplasia. Quiescent smooth muscle cells divide less rapidly, do not secrete significant amounts of extracellular matrix, and promote healing and reformation of an intact endothelial layer over the neointimal layer. Additionally, the duty cycles and pulse repetition frequencies of the treatment will be selected to limit the heating within the neointimal layer to a temperature rise below 10° C., preferably below 5° C., and more preferably below 2° C. Such limited temperature rise further assures the viability and normalcy of the treated cells to enhance healing and re-endothelialization of the neointimal layer in a rapid manner.

Thus, the present invention can provide a number of related treatments and therapies. In a broad sense, the methods of the present invention can be used to treat virtually any arterial injury at risk of hyperplasia to both limit the extent of neointimal hyperplasia and promote the rapid and complete healing of an endothelial layer over the neointimal layer. Additionally, the methods of the present invention can be performed as part of a treatment method for stenotic arterial disease, where the vibrational energy will be employed in conjunction with a primary recanalization technique, typically balloon angioplasty, atherectomy, laser angioplasty, and the like. In such treatments, the vibrational energy may be applied sequentially, concurrently, or both sequentially and concurrently. For example, in the case of balloon angioplasty, a vibrational transducer could be located within the angioplasty balloon to apply vibrational energy both during and after the arterial dilatation. Additionally, the present invention will find particular use in conjunction with stent placement. The use of stents is itself a secondary treatment to inhibit restenosis following angioplasty or other primary recanalization treatments. While stents are very effective in preventing abrupt reclosure and late negative remodeling, they are generally much less effective in preventing neointimal hyperplasia. Indeed, the placement of a stent following angioplasty can in at least some instances promote neointimal hyperplasia when compared to angioplasty alone. Thus, by applying vibrational energy according to the methods of the present invention either before or shortly after stent placement, the long-term patency of stents can be greatly improved. Moreover, it may be desirable in some instances to select both the frequency of the vibratory energy and the resonance properties of the stent so that the stent may be driven in at its resonant frequency to enhance and/or distribute the vibratory energy to the arterial wall in a manner which is superior to the delivery of vibratory energy.

Mechanical index and duration of the treatment are the most important treatment perimeters. The mechanical index (MI) is a function of both the intensity and the frequency of the vibrational energy produced, and is defined as the peak rarefactional pressure (P) expressed in megaPascals divided by the square root of frequency (f) expressed in megaHertz:

$$MI = \frac{P}{\sqrt{f}}$$

The duration of treatment is defined as the actual time during which vibrational energy is being applied to the arterial wall. Duration will thus be a function of the total elapsed treatment time, i.e., the difference in seconds between the initiation and termination of treatment; burst length, i.e., the length of time for a single burst of vibrational energy; and pulse repetition frequency (PRF). Usually, the vibrational energy will be applied in short bursts of high intensity (power) interspersed in relatively long periods of no excitation or energy output. An advantage of the spacing of short energy bursts is that heat may be dissipated and operating temperature reduced.

Broad, preferred, and exemplary values for each of these perimeters is set forth in the following table.

PREFERRED AND EXEMPLARY TREATMENT CONDITIONS

| | BROAD | PREFERRED | EXEMPLARY |
|---|---|---|---|
| Mechanical Index (MI) | 0.1 to 50 | 0.2 to 10 | 0.5 to 5 |
| Intensity (SPTA, W/cm$^2$) | 0.01 to 100 | 0.1 to 20 | 0.5 to 5 |
| Frequency (kHz) | 100 to 5000 | 300 to 3000 | 500 to 1500 |
| Elapsed Time (sec.) | 10 to 900 | 30 to 500 | 60 to 300 |
| Duty Cycle (%) | 0.1 to 100 | 0.2 to 10 | 0.2 to 2 |
| Pulse Repetition Frequency (PRF)(Hz) | 10 to 10,000 | 100 to 5000 | 300 to 3000 |

The vibrational energy will usually be ultrasonic energy applied intravascularly using an intravascular catheter having an interface surface thereon, usually near its distal end. The catheter will be intravascularly introduced so that the interface surface lies proximate the target region to be treated.

Preferably, the ultrasonic or other vibrational energy will be directed radially outward from an interface surface into a target site or region within the arterial wall. By "radially outward," it is meant that the compression wave fronts of the vibrational energy will travel in a radially outward direction so that they enter into the arterial wall in a generally normal or perpendicular fashion. It will generally not be preferred to direct the vibrational energy in a direction so that any substantial portion of the energy has an axial component.

In most instances, it will be desirable that the vibrational energy be distributed over an entire peripheral portion or section of the arterial wall. Such peripheral portions will usually be tubular having a generally circular cross-section (defined by the geometry of the arterial wall after angioplasty, stenting, or other recanalization treatment) and a length which covers at least the length of the treated arterial wall. While it may be most preferred to distribute the vibrational energy in a peripherally and longitudinally uniform manner, it is presently believed that complete uniformity is not needed. In particular, it is believed that a non-uniform peripheral distribution of energy over the circumference of the arterial wall will find use, at least so long as at least most portion of walls are being treated.

Even when vibratory forces are spaced-apart peripherally and/or longitudinally, the effective distribution of vibrational energy will be evened out by radiation pressure forces arising from the absorption and reflection of ultrasound on the circumferential walls of the arterial lumen, thereby producing a uniform effect due to the fact that the tension in the wall of the lumen will tend to be equal around its circumference. Accordingly, a uniform inhibitory effect can occur even if there is some variation in the intensity of the ultrasound (as in the case of the non-isotropic devices described hereinafter). This is due to the fact that the tension around the circumference of the lumen will be equal in the absence of tangential forces.

Usually, the interface surface will be energized directly or indirectly by an ultrasonic transducer which is also located at or near the distal tip of the catheter. By direct, it is meant that the surface is part of the transducer. By indirect, it is meant that the transducer is coupled to the surface through a linkage, such as a resonant linkage as described hereinafter. Alternatively, energy transmission elements may be provided to transfer ultrasonic energy generated externally to the catheter to the interface surface near its distal tip. As a further alternative, although generally less preferably, the ultrasonic energy may be generated externally and transmitted to the target region by focusing through the patient's skin i.e., without the use of a catheter or other percutaneously introduced device. Such techniques are generally referred to as high intensity focused ultrasound (HIFU) and are well described in the patent and medical literature.

When employing an intravascularly positioned interface surface, the surface may directly contact all or a portion of the blood vessel wall within the target region in order to effect direct transmission of the ultrasonic energy into the wall. Alternatively, the interface surface may be radially spaced-apart from the blood vessel wall, wherein the ultrasonic energy is transmitted through a liquid medium disposed between the interface surface and the wall. In some cases, the liquid medium will be blood, e.g., where the interface surface is within an expansible cage or other centering structure that permits blood flow therethrough. In other cases, the liquid medium may be another fluid either contained within a balloon which circumscribes the transducer and/or contained between axially spaced-apart balloons which retain the alternative fluid. Suitable ultrasonically conductive fluids include saline, contrast medium, and the like. In some cases, the medium surrounding the interface surface will include drugs, nucleic acids, or other substances which are intended to be intramurally delivered to the blood vessel wall. In particular, the delivery of nucleic acids using intravascular catheters while simultaneously directly inhibiting cell proliferation and hyperplasia is described in co-pending Application No. 60/070,073, assigned to the assignee of the present application, filed on the same day as the present application, the full disclosure of which is incorporated herein by reference.

Ultrasonic or other vibrational excitation of the interface surface may be accomplished in a variety of conventional ways. The interface surface may be an exposed surface of a piezoelectric, magnetostrictive, or other transducer which is exposed directly to the environment surrounding the catheter. Alternatively, the transducer may be mechanically linked or fluidly coupled to a separate surface which is driven by the transducer, optionally via a resonant linkage, as described in co-pending application Ser. Nos. 08/565,575; 08/566,740; 08/566,739; 08/708,589, 08/867,007; and 09/223,225, the full disclosures of which have previously been incorporated herein by reference. Preferably, the interface surface may be vibrated in a generally radial direction in order to emit radial waves into the surrounding fluid and/or directly into the tissue. Alternatively, the interface surface may be vibrated in a substantially axial direction in which case axial waves may be transmitted into the surrounding environment and/or directly into the blood vessel wall.

The methods of the present invention may further comprise the primary treatment of an occlusion within a blood vessel in order to widen or recanalize the blood vessel. Suitable primary treatments include angioplasty, atherectomy, stenting, laser angioplasty, thermal angioplasty, and the like. Following the primary treatment, the treated region may be exposed to ultrasonic vibrational energy as generally described above.

Usually, however, it will be desirable to place a stent within the recanalized region as a further part of the present invention. The vibrational energy may be applied before implantation of the stent, during implantation of the stent, or following stent implantation.

The present invention further provides improved methods of the type where intravascular hyperplasia is inhibited by the application of energy, such as the application of radiation from radioisotopes, x-rays sources, or the like. The improvement herein comprises the application of ultrasonic energy to the blood vessel wall in place of the other energy sources.

The present invention still further comprises systems including a catheter having an interface surface and a power source connectable to the catheter. The power source will be adapted to energize the interface surface according to any of the methods set forth above.

The present invention still further comprises kits including a catheter having an interface surface. The kits further include instructions for use according to any of the methods set forth above. Optionally, the kits may still further include a conventional package, such as a pouch, tray, box, tube, or the like. The instructions may be provided on a separate printed sheet (a package insert setting forth the instructions for use), or may be printed in whole or in part on the packaging. A variety of other kit components, such as drugs to be delivered intravascularly through the catheter, could also be provided. Usually, at least some of the components of the system will be maintained in a sterile manner within the packaging.

BRIEF DESCRIPTION OF THE DRAWINGS

FIGS. 10A, 10B, 11A, 11B, 12A, 12B, 13A and 13B are histological slices of US treated and non-treated artery pairs, as described in detail in the Experimental section hereinafter. The A panels are the treated vessel while the B panels are the untreated controls.

DESCRIPTION OF THE SPECIFIC EMBODIMENTS

Figure 1A:
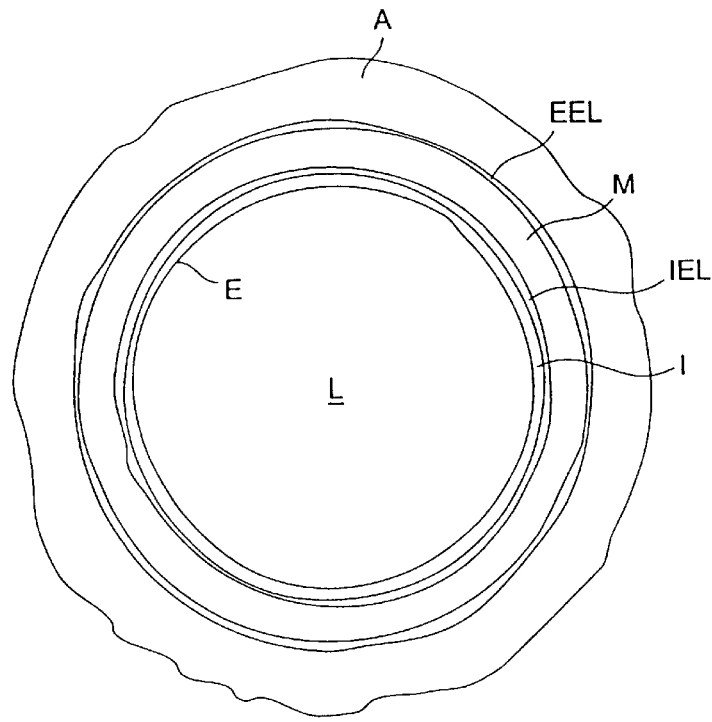
FIGS. 1A–1E are schematic cross-section illustrations of an artery at different stages of health and treatment.

FIG. 1A illustrates a cross-sectional view of a healthy artery, such as a coronary artery, an internal carotid artery, femoral artery, or other artery of the type which is subject to arteriosclerosis. The arterial structure comprises a number of lamina which surround the arterial lumen L, including the outermost adventitial layer A. Immediately inside of the adventitial layer is the external elastic lamina EEL which in turn surrounds the medial layer M. Inside of the medial layer is the internal elastic lamina IEL, and inside of the internal elastic lamina is the intimal layer I. The endothelial layer E lines the interior of the intimal layer, and the intimal layer and endothelial layer will normally be relatively thin in a healthy artery, as illustrated in FIG. 1A.

Figure 1B:
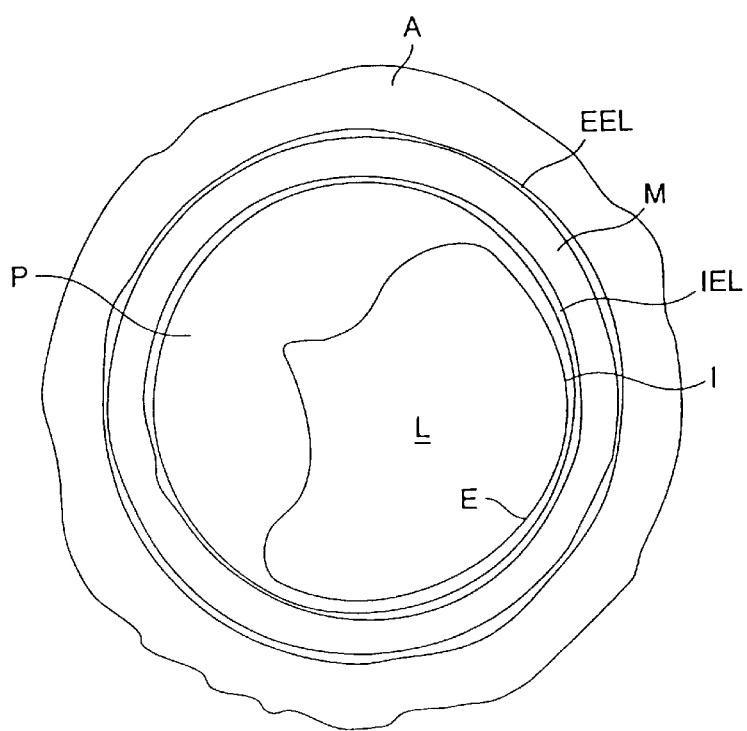

FIG. 1B illustrates an artery suffering from atherosclerosis, which is the most significant form of arteriolosclerosis. In the early stages of atherosclerosis, the arterial intimal layer thickens with deposits called atheromas or atherosclerotic plaques. The arterial wall compensates by expanding to reduce the loss of luminal cross-sectional area. After the intimal layer thickens significantly, the arterial wall can no longer compensate, and the luminal area is reduced, resulting in total occlusion in the worst cases. Even when the lumen remains partly open, the artery is at significant risk of total occlusion or arterial spasm caused by emboli or other events which would not affect a healthy artery.

Figure 1C:
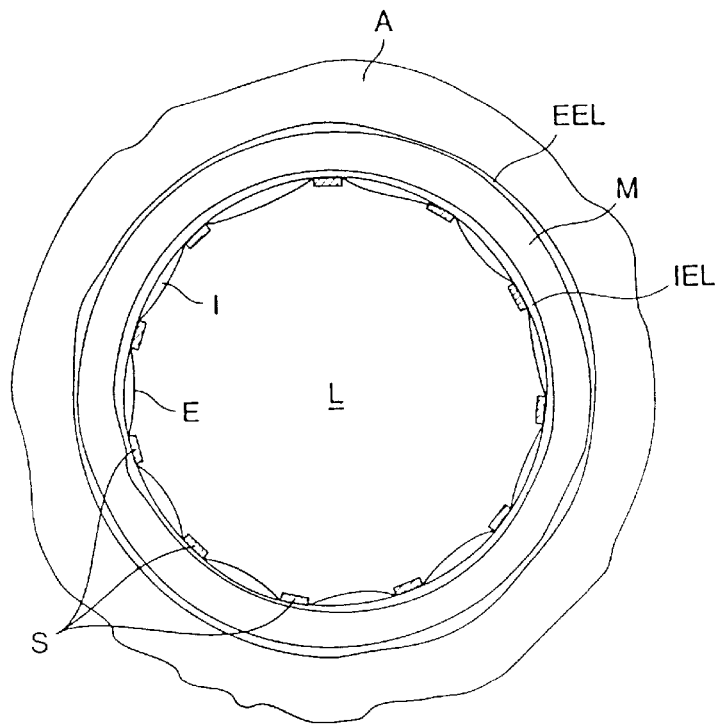
Figure 1D:
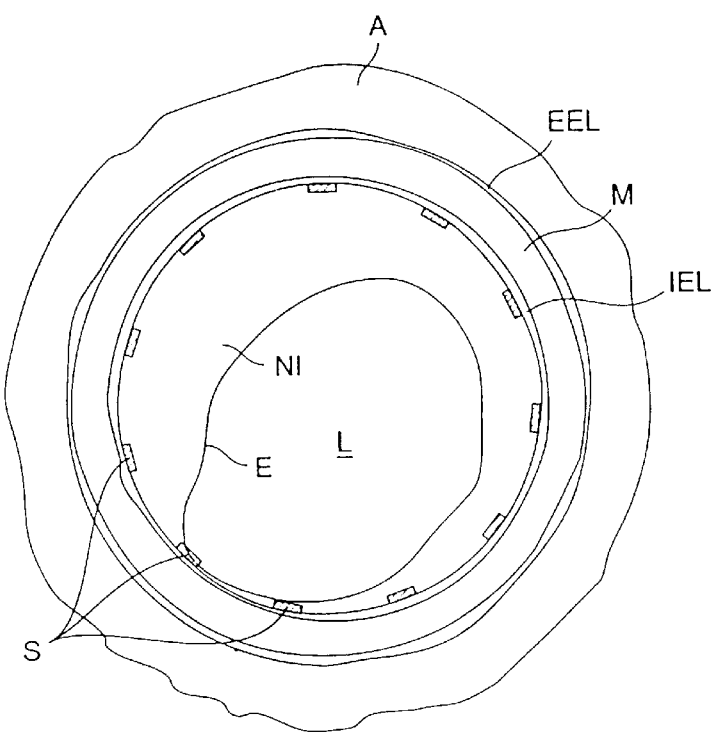

Atherosclerosis can be treated by a number of techniques described in the Background section above. The present invention is concerned primarily with intravascular recanalization techniques, such as balloon angioplasty, laser angioplasty, atherectomy, and the like. Of particular interest, balloon angioplasty is frequently followed by placement of a stent S, as illustrated in FIG. 1C. Balloon angioplasty is very effective at widening the arterial lumen, but subject to both abrupt and long-term restenosis, i.e., reclosing of the arterial lumen. The use of a stent is highly effective at preventing abrupt closure and negative remodeling (both short term events) but has been found to be less effective in preventing long-term restenosis, such as that due to intimal hyperplasia, as illustrated in FIG. 1D. It is presently believed that intimal hyperplasia occurs as the result of arterial tissue injury caused by the primary recanalization technique, particularly balloon angioplasty, as well as stent placement. Injury occurs both to the intimal layer as well as the medial layer and can cause an exaggerated or excessive healing response characterized by excessive proliferation of the vascular smooth muscle cells in the neointima and subsequent secretion of extracellular matrix causing intimal hyperplasia that can often result in restenosis of the artery. While the mechanism is complex, the hyperplasia appears to result at least partly from transformation of the smooth muscle cells from a quiescent, contractile phenotype to a proliferative phenotype. The proliferation of smooth muscle cells which can result from such transformation appears to peak at about seven days after the initial treatment and can last for many weeks. The subsequent secretion of extracellular matrix from the proliferating smooth muscle cells producers the hyperplasia which becomes significant at about 28 days following the initial injury, as shown in FIG. 1D. If untreated, such secretion can continue well after the 28 day period.

The present invention utilizes vibrational energy, particularly ultrasonic energy having the characteristics described above, to promote healing of the vascular injuries caused by recanalization and to inhibit intimal hyperplasia, particularly the hyperplasia associated with excessive proliferation of vascular smooth muscle cells. The healing response provided by the present invention is presently believed to provide a number of beneficial therapeutic effects, including rapid formation of a healed, morphologically normal endothelial layer over the neointima. In addition, the healing response is preferably associated with reduced formation of extracellular matrix, reduced intramural fibrin deposition, and reduced chronic inflammation response. Such beneficial responses, together with the reduced proliferation of vascular smooth muscular cells, is believed to be responsible for the reduction in neointimal hyperplasia observed as a result of the treatment methods of the present invention.

Figure 1E:
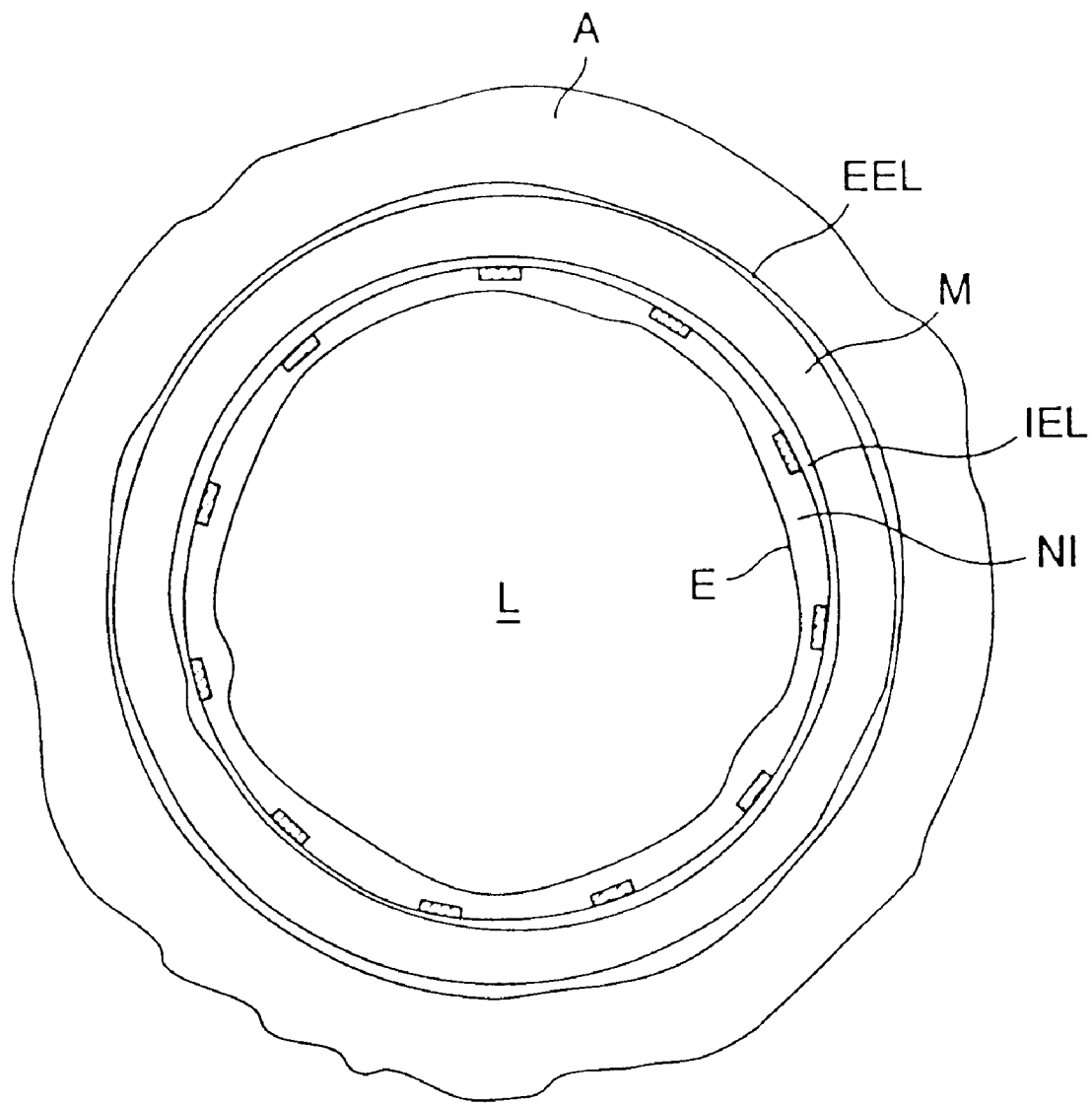

Regardless of the exact mechanisms responsible for this reduction in neointimal hyperplasia, the methods of the present invention can provide a healed neointimal layer NI having a substantially reduced thickness, as shown in FIG. 1E, in comparison to untreated controls, as shown in FIG. 1D. The reduction in average cross-sectional area of the neointimal layer will usually be at least 10%, preferably being at least 20%, and often being at least 30% or greater. The improved healing of the neointimal layer results in substantially complete coverage of the neointima with endothelial cells and a subendothelial layer formed for the most part by quiescent smooth muscle cells. Such healing helps assure that the arterial wall is less subject to thrombosis and restenosis then is the case with untreated arteries and arteries treated with other techniques, such as ionizing radiation.

Figure 2A:
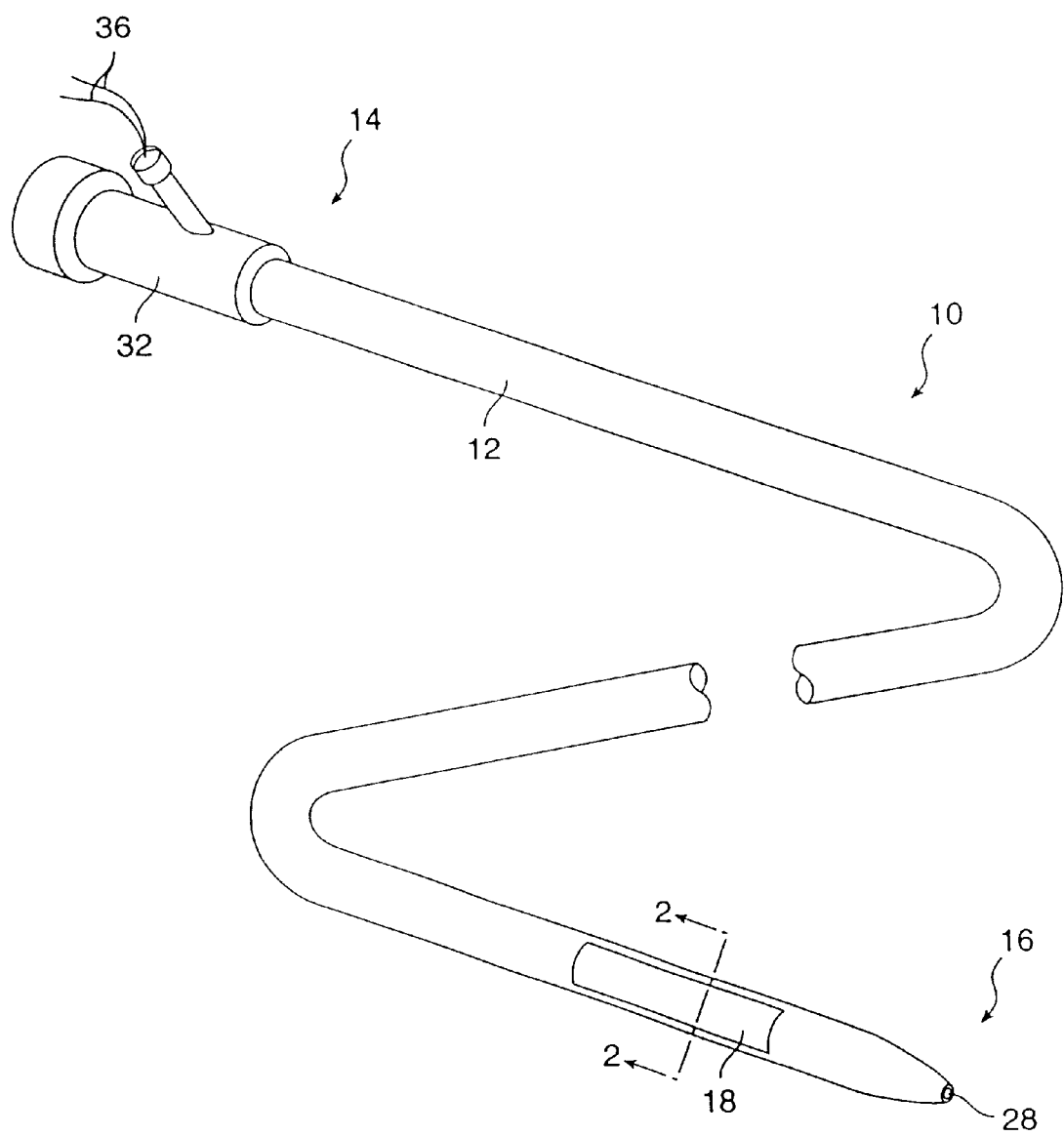
FIG. 2A is a perspective view of an ultrasonic catheter suitable for use in the methods of the present invention.
Figure 2B:
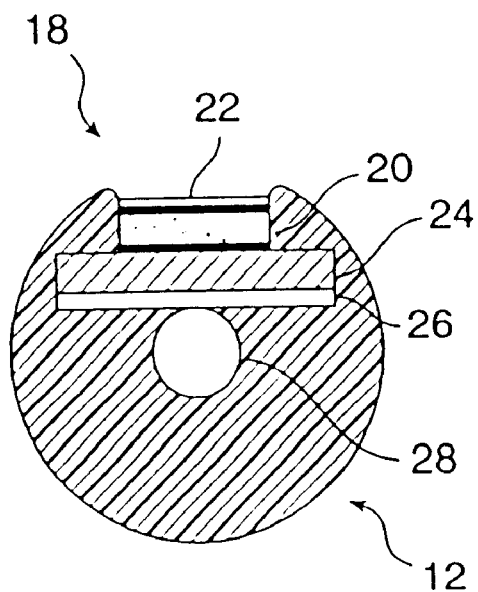
FIG. 2B is a cross-sectional view taken along line 2—2 of FIG. 2A.

An exemplary catheter 10 suitable for performing methods according to the present invention is illustrated in FIGS. 2A and 2B. Catheter 10 comprises a catheter body 12 having a proximal end 14 and a distal end 16. An ultrasonically-driven interface surface 18 is disposed in a window near the distal end 16 of the catheter body 12. As illustrated, the interface surface 18 comprises a piezoelectric ceramic transducer 20 having an exposed surface coated with an insulating layer 22. The dimensions and materials of the piezoelectric ceramic will be chosen to permit actuation at the frequencies and power levels described above. Typically, the ceramics will be relatively thin, and will be backed with an aluminum shim 24 disposed over an air gap 26. Such air-backed transducer assemblies are particularly suitable for high frequency operation, typically with frequencies above 1 MHz. Catheter body 12 will further comprise at least one lumen 28 for delivery over a guidewire in a conventional manner. The piezoelectric transducer 20 may be driven by connection to a conventional signal generator and power amplifier through wires 30 which exit through a proximal hub 32.

Figure 3:
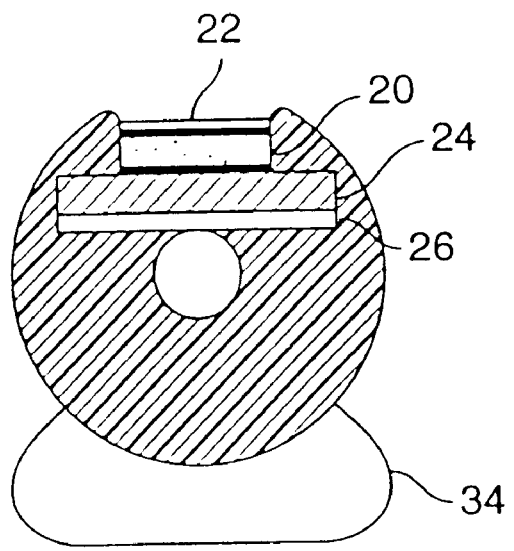
FIG. 3 is a first alternative cross-sectional view.

The piezoelectric ceramic transducer 20 vibrates in all three orthogonal directions as is the nature of piezoelectric materials. For the purposes of the present catheter design, however, the primary vibrational mode is in the radial direction, i.e., energy is directed in radially emanating waves away from the interface surface 18. Such radial waves may be transferred into the blood or other medium surrounding the distal end of the catheter. Alternatively, the surface 22 may be directly engaged against the blood vessel wall. To do so, it may be desirable to employ a lateral urging means, such as a balloon 34 as illustrated in FIG. 3. All other aspects of the catheter of FIG. 3 are the same as illustrated in FIGS. 2A and 2B.

Figure 4:
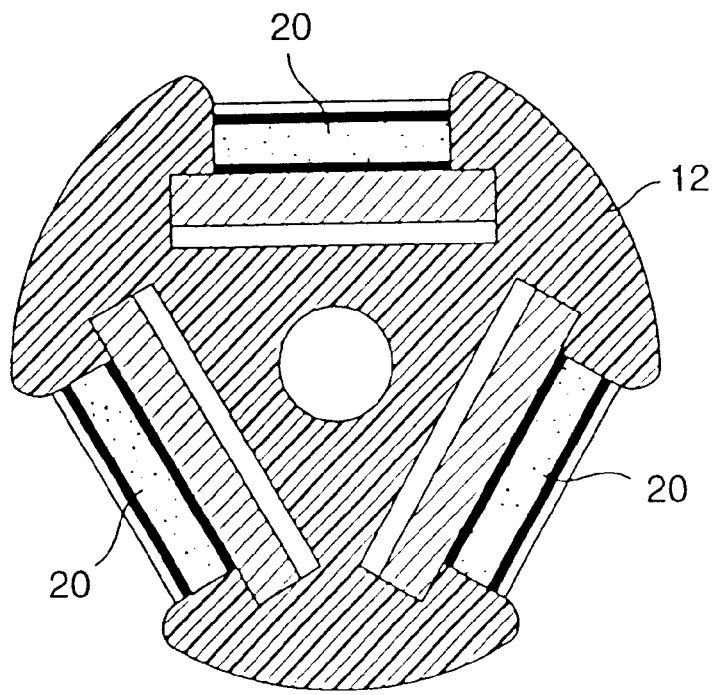
FIG. 4 is a second alternative cross-sectional view.

Other transducer configurations will also be possible. As illustrated in FIG. 4, a plurality of transducers 20 could be circumferentially spaced-apart about the exterior of the catheter body 12. In this way, energy can be transmitted radially outwardly in multiple directions at once. In order to enhance the uniformity of the treatment, the catheter could optionally be rotated while the energy is being delivered. In order to further enhance the uniformity of ultrasonic energy being radiated outwardly, the multiple transducer embodiments can be driven by a multiplexed power source.

Figure 5:
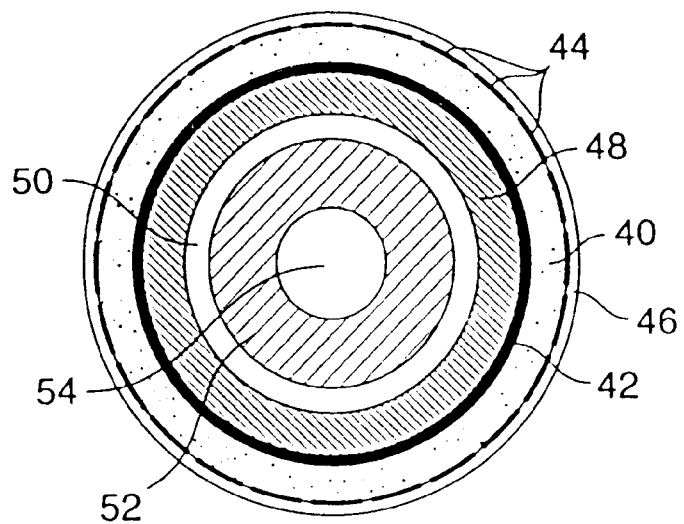
FIG. 5 is a third alternative cross-sectional view.

To further enhance the uniformity of ultrasonic energy being delivered, a piezoelectric transducer 40 can be formed in a cylindrical geometry, as illustrated in FIG. 5. The piezoelectric ceramic transducer 40 can be driven by inner and outer electrodes 42 and 44, and the outer electrodes coated by a thin insulating layer 46. A transducer can be supported on a suitable cylinder, such as an aluminum cylinder 48, and for high frequency operation an air gap 50 may be provided. The transducer can be mounted symmetrically about catheter body 52 having a conventional guidewire lumen 54.

In all of the above cases, the dimensions of the transducer(s) will depend in large part on the frequency of operation as well as the catheter size. The width of the transducers will typically be in the range from 0.1 mm to 6 mm, usually from 0.5 mm to 3 mm. The length of the transducer may vary from 1 mm to 2 or more cm, with the length being primarily limited by loss of flexibility of the distal end of the catheter. Multiple transducer elements could also be provided along the length of the catheter, i.e., being axially spaced-apart, as described in more detail below.

Figure 6A:
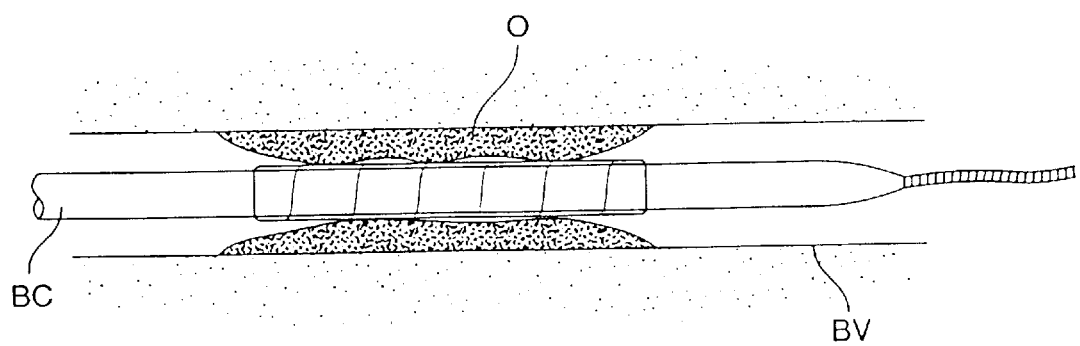
FIGS. 6A–6D illustrate use of the catheter of FIG. 1 in performing a method according to the present invention.
Figure 6B:
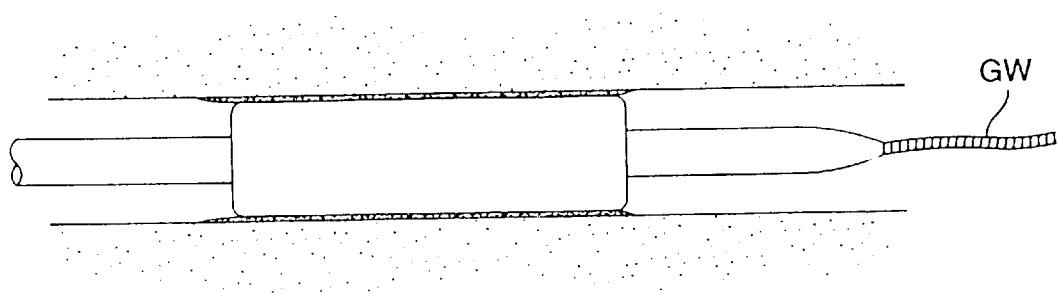

Methods according to the present invention for treating a primary vascular occlusion will be described with reference to FIGS. 6A–6D. An angioplasty balloon catheter BC may be used to treat a primary occlusion O in a coronary artery or other blood vessel BV. The balloon is expanded to widen in the occlusion, as shown in FIG. 6B, thereafter the catheter 10 may be introduced over the same guidewire GW. The transducer 20 (not visible in FIG. 6C) is actuated and radiates ultrasonic energy toward a region of the blood vessel wall which was previously treated by the balloon angioplasty. The frequency and intensity of the treatment are generally as set forth above. The treatment time may vary from several seconds to 10 minutes or more, typically being in the range from 20 seconds to 3 minutes.

Figure 6C:
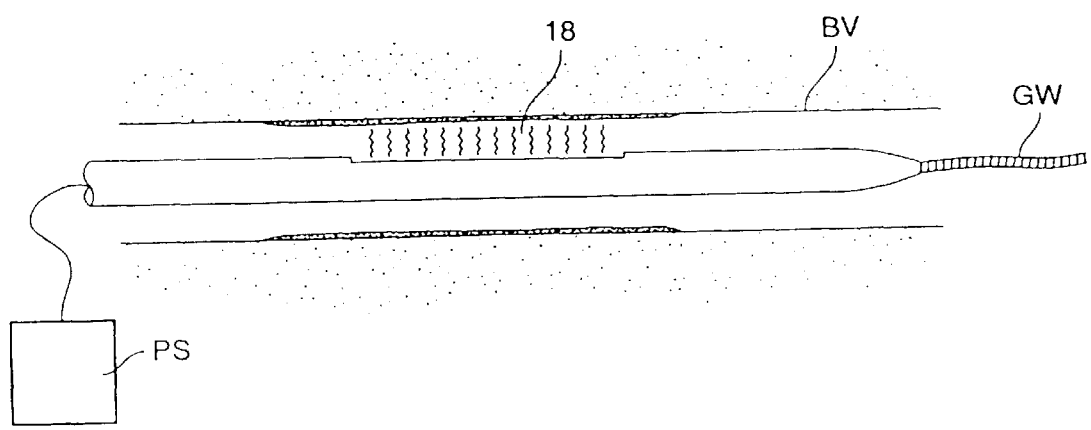
Figure 6D:
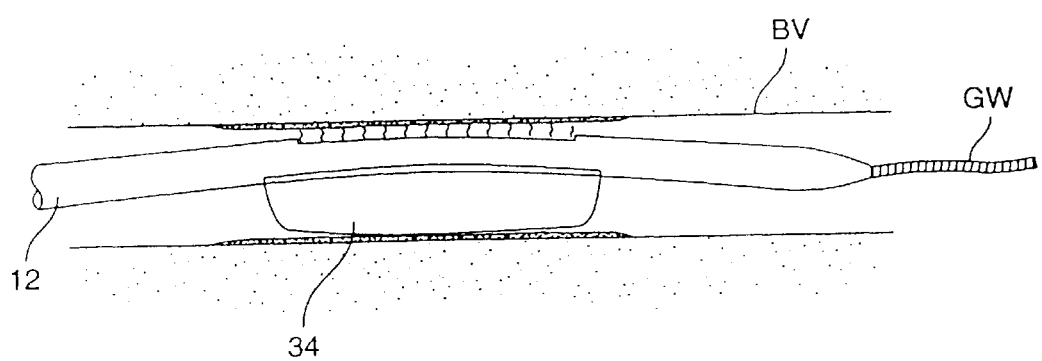

As shown in FIG. 6C, the catheter is free to move radially within the blood vessel lumen. Thus, the intensity of energy applied to the blood vessel wall will not be completely controlled. In many cases, it will be desirable to position the catheter in a known manner within the blood vessel wall. For example, an asymmetric balloon 34 (FIG. 3) may be used to laterally engage the interface surface against a portion of the blood vessel wall, as shown in FIG. 6D. Other positioning means, such as concentric balloons, axially spaced-apart balloons, positioning cages, positioning wires, and the like, may be utilized for positioning the catheter within the blood vessel lumen.

Figure 7:
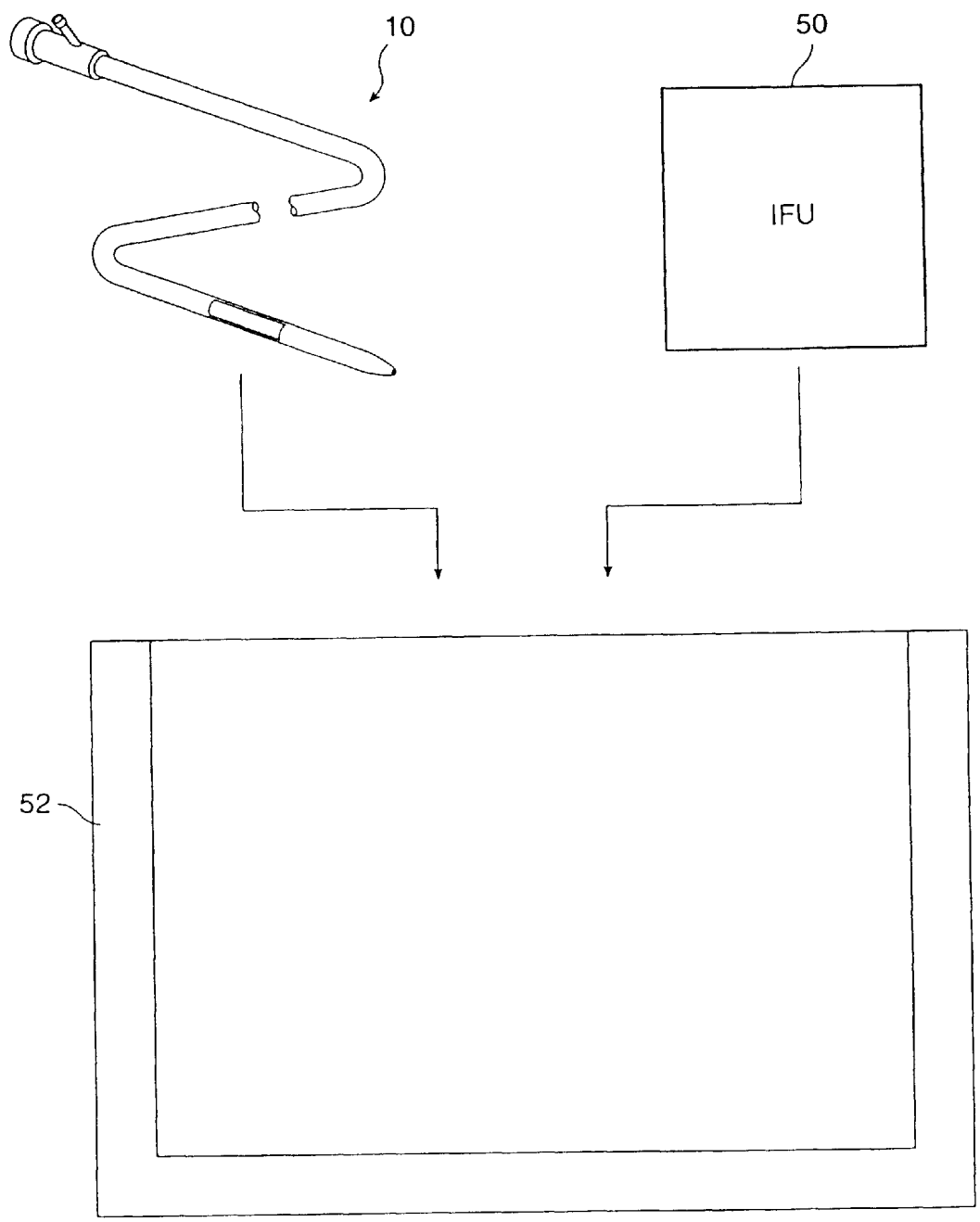
FIG. 7 illustrates a kit incorporating a catheter and instructions for use according to the present invention.

The catheters 10 of the present invention will usually be packaged in kits, as illustrated in FIG. 7. In addition to the catheter 10, such kits will include at least instructions for use 50 (IFU). The catheter and instructions for use will usually be packaged together within a single enclosure, such as a pouch, tray, box, tube, or the like 52. At least some of the components may be sterilized within the container. Instructions for use 50 will set forth any of the methods described above. The kits may include a variety of other components, such as drugs or other agents to be delivered by the catheter to enhance the therapy.

Figure 8:
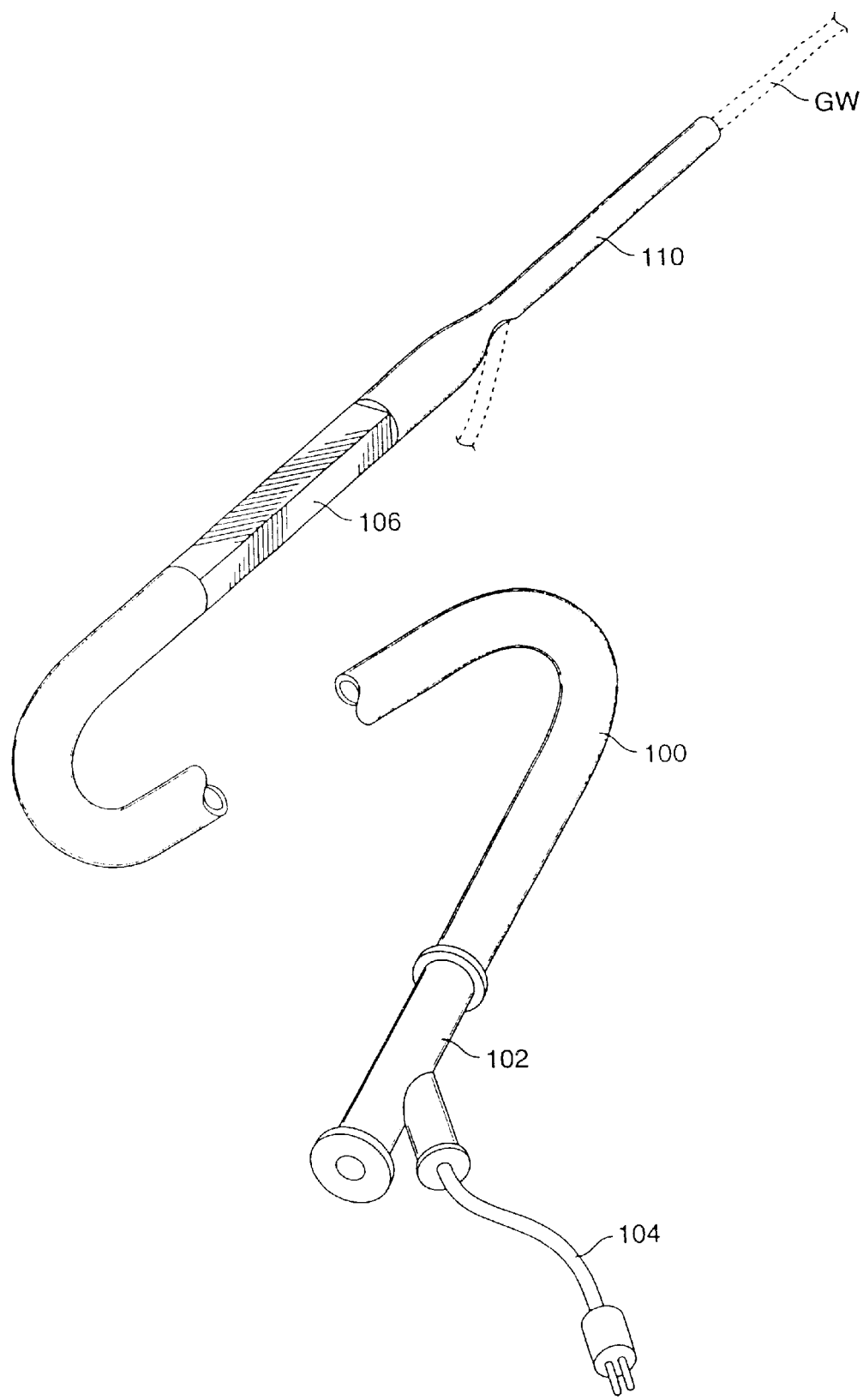
FIG. 8 illustrates a specific catheter construction in accordance with the principles of the present invention, which catheter was used in the examples reported in the Experimental section hereinafter.

Referring to FIG. 8, an exemplary catheter 100 useful for performing the methods of the present invention will be described. The catheter body has a length of 120 cm and is formed as a single lumen polymeric extrusion. A hub 102 at a proximal end of the catheter has an electrical connector 104 for attaching a piezoelectric ceramic transducer 106 to a suitable power supply. The transducer has dimensions of 0.08 in×0.08 in×0.4 in, and can operate at the frequency, power, etc. set forth in the Experimental section hereinafter. The catheter has a guidewire lumen in its distal tip 110 for permitting intravascular placement over a separate guidewire GW. This catheter was constructed and used in the examples set forth in the Experimental section hereinafter. A wide variety of other catheters suitable for use in the present invention are set forth in copending application Ser. No. 09/223,225, the full disclosure of which has previously been incorporated by reference.

The following examples are offered by way of illustration, not by way of limitation.

EXPERIMENTAL

Materials and Methods

Study Protocol

A total of 23 anesthetized and artificially ventilated domestic swine (45.5±12.7 kg) were catheterized through the left or right carotid artery. Both external and internal femoral arteries were imaged with an intravascular ultrasound (IVUS) catheter (Hewlett-Packard, Ultracross®) for the measurements of vessel size. Mean vessel diameter (minimum lumen diameter+maximum lumen diameter)/2 was used to calculate the target balloon-to-artery (b/a) ratio (1.4) for balloon overstretch injury. Balloon injury was created by three consecutive 60 sec balloon dilatations with a compliant Cordis Powerflex PTA balloon (either 5.0 or 6.0 mm in diameter, 20 mm length). In the stented arteries, after each balloon injury, a hand crimped biliary stent (P204 Jonhson & Johnson) was deployed at the injury site using the same pressure as used for the overstretch injury and using two 30 sec inflations. After either balloon injury only or after balloon injury combined with stent injury, internal and external femoral arteries were divided to receive either US therapy or sham treatment. Pigs were followed up for either 7 days, bromodeoxyuridine (BrdU) group, to study the effect of ultrasound (US) therapy on smooth muscle cell proliferation, or 28 days, to study the effects of US therapy on intimal hyperplasia in either balloon injured arteries or in balloon and stent injured arteries.

Ultrasound treatment (URx): Stented arteries were randomly treated or sham treated with a tip mounted therapeutic ultrasound catheter (FIG. 8). In the BrdU group, US therapy was delivered for a total exposure time of either 12 sec (12USG, number of treated arteries n=2), 120 sec (120USG, n=6) or 300 sec (300USG, n=5) per location within the injured artery without causing significant cavitation or a significant rise in temperature. The 7 day match controlled sham treated arteries were exposed to the non-energized US catheter for either 120 sec (120CG, n=3) or 300 sec (300CG, n=3). In the 28 day stented group, ultrasound therapy was delivered for a total exposure time of 120 sec per location in both control group (28CG, n=12) and US therapy group (28USG, n=12). In the 28 day balloon treated group, the arteries were exposed to a non-energized or energized US catheter for 300 sec per location in both sham treated control group (BCG, n=9) and ultrasound treated group (BUSG, n=9).

Ultrasound treatment methods: Three ultrasound treatment regimes were defined for this series of studies. The nominal conditions for the USG12 group were 12 seconds duration, 600 kHz ultrasound frequency, 10 cycle burst and 500 Hz pulse repetition frequency at 180 W/cm$^2$ spatial-peak pulse-average intensity. For the USG120 and 28USG groups, the conditions were identical to the USG12 group, except that the duration of exposure was increased to 120 seconds. The nominal conditions for the USG300 and 28BUSG groups were 300 seconds duration, 600 kHz ultrasound frequency, 20 cycle burst and 1 kHz pulse repetition frequency at 180 W/cm$^2$ spatial-peak pulse-average intensity. Under all three of these treatment regimes, the tissue heating due to ultrasound energy absorption was predicted to be less than 2° C.

In several cases, the heating of the transducer due to electro-mechanical losses within the device itself would have been significantly greater than the tissue heating due to absorption of ultrasound energy. The heat from the transducer would warm the surrounding tissue through perfusion and through thermal conduction and convection. The temperature rise of the transducer would be greatest when the catheter and/or spasm in the vessel impeded blood flow. To estimate the transducer temperature rise under various conditions of perfusion, a small thermocouple was attached to the transducer surface. To model the condition of flowing blood, the transducer was placed inside a 9 mm silicone tube, suspended within a water tank, with 1 liter/minute of water flow supplied by a pump. It was estimated that this condition would be comparable to 150 ml/minute blood flow in a 4 mm artery in terms of the cooling effect of the fluid flow. To estimate the transducer temperature rise without perfusion, the catheter was placed inside a 4 mm plastic tube, suspended within a water tank, but without flow through the tube. The results of these measurements are summarized in Table 1.

TABLE 1

The effect of ultrasound condition and flow (150 ml/min)/no flow on the temperature of ultrasound transducer face in a 4 mm diameter plastic tube

| US condition | exposure time (sec) | flow | temperature rise (° C.) |
|---|---|---|---|
| 180 W/cm$^2$ | 120 | yes | 2.0 |
| | 120 | no | 10.0 |
| | 300 | yes | 6.0 |
| | 300 | no | 23.0 |

Stented arteries were randomly selected for either sham treatment or ultrasound exposure using an 8 Fr catheter with an ultrasound transducer mounted approximately 5 cm proximal to the tip. The transducer consisted of a bar-shaped piezoelectric ceramic element, approximately 1 cm in length and with a 2 mm square cross section. The radiation pattern from this device has four broad lobes, one corresponding to each face of the transducer, with nulls in between these lobes on the diagonals with respect to the square cross section of the transducer. In every group, including the sham exposure groups, the catheter was typically positioned at five locations longitudinally within the artery. The treatment extended beyond the ends of the stent or balloon injury site and the treatments overlapped such that there were no gaps in ultrasound exposure within the region of interest.

Each catheter was tested for acoustic output using a calibrated needle hydrophone in a room temperature water bath. The beam pattern from these devices is quite non-uniform, and the ultrasound signal strength diminishes significantly with distance from the transducer. To characterize the performance of these devices in a consistent manner, the highest output from any location on any of the transducer faces was found. The spatial-peak output was measured as close as possible to the surface of the transducer at this location. It was generally observed that the variation in output over the surface of the transducer was within approximately ±1 dB relative to the average. From this testing, the optimum operating frequency was determined (typically 550 to 700 kHz) and a calibration coefficient was derived relating the acoustic output to the electrical excitation.

The ultrasound instrumentation system consists of three main components: a function generator for generating sine-wave tone bursts, an RF amplifier capable of amplifying the tone bursts up to 1 $kV_{P-P}$ amplitude, and an oscilloscope for monitoring the voltage and current to the device. The required electrical parameters were determined from the transducer calibration data to provide the desired nominal acoustic exposure amplitude, frequency, pulse repetition frequency and burst length, and the function generator was programmed accordingly. In the course of the treatments, the electrical excitation was monitored and recorded so that the actual ultrasound exposure level could be estimated.

Cell proliferation: BrdU is an analog to thymidine, which is incorporated into the DNA during the S phase of the cell cycle. Immunohistochemical staining with BrdU is an accurate method for measuring cell proliferation. The 7-day animals were treated with BrdU (5-Bromo-2'-deoxyuridin, Sigma) 24 hours before sacrifice in order to calculate the amount of proliferating cells within the intima. Animals were sacrificed at 7 days and treated arteries were pressure fixed via the descending aorta with 10% formaldehyde for at least 15 minutes. Each histological analysis included three section sites from within each stent (proximal, mid and distal site of the stent). Total number of cells/area, the amount of BrdU labeled cells and the % of BrdU labeled cells was calculated from each site.

Intimal hyperplasia: The effect of ultrasound treatment on intimal hyperplasia was studied one-month post injury. After the animals were sacrificed, femoral arteries were pressure fixed for a minimum of 15 min via the descending aorta. Histological analysis was based on standard H&E staining. Measured parameters were: external elastic lamina circumference and area, (EEL, cm and $mm^2$), internal elastic lamina circumference and area (IEL, cm and $mm^2$), medial area (MA=EEL $mm^2$–IEL $mm^2$, $mm^2$), lumen area (LA, $mm^2$), vessel area (VA=EEL $mm^2$), neointimal area (NA=IEL $mm^2$–LA $mm^2$, $mm^2$), neointimal thickness over and between the stent struts (measured at 5 random sites), mean neointimal thickness (the average of every second stent), the amount of intramural fibrin/red blood cells, chronic inflammatory cells and IEL disruption (0=none, 1=minimal, 2=mild, 3=moderate, 4=severe) or the % of missing arch of the IEL. The arterial lamina are illustrated schematically in FIG. 1A.

Statistical Analysis

All statistical analyses were performed using Statview software. Results are expressed as mean ±SD unless otherwise indicated. Student's t-test was used to calculate the significance of difference between ultrasound and sham treatment within each group in cell proliferation and intimal hyperplasia. Mann Whitney U nonparametric test for unpaired data was used on ranks of ordered variable of fibrin/RBC content, chronic inflammation and IEL disruption (0=none, 1=minimal, 2=mild, 3=moderate and 4=severe). Differences were considered significant when $p<0.05$.

Results

The baseline experimental settings were similar in each study group (Table 2). The average weight of the animals was 43 kg and mean vessel diameter was 4.1 mm. Also balloon/artery (b/a) ratio and balloon inflation pressures were very similar.

TABLE 2

The baseline experimental settings of different study groups (mean ± SD)

| group | weight (kg) | mean vessel diameter (mm) | b/a ratio | inflation ATM |
|---|---|---|---|---|
| % BrdU study | | | | |
| CG (n = 18) | 47.4 ± 13.7 | 4.0 ± 0.4 | 1.4 ± 0.1 | 9.5 ± 2.3 |
| USG (n = 39) | 47.4 ± 12.6 | 4.1 ± 0.5 | 1.3 ± 0.3 | 10.0 ± 13.0 |
| stent study | | | | |
| CG (n = 12) | 43.8 ± 11.3 | 4.2 ± 0.3 | 1.4 ± 0.1 | 9.7 ± 2.2 |
| USG (n = 12) | 42.8 ± 11.4 | 4.2 ± 0.3 | 1.4 ± 0.1 | 10.6 ± 1.9 |
| balloon study | | | | |
| CG (n = 9) | 39.0 ± 4.1 | 4.1 ± 0.3 | 1.4 ± 0.0 | 8.6 ± 2.9 |
| USG (n = 9) | 39.1 ± 4.1 | 4.2 ± 0.3 | 1.4 ± 0.0 | 10.7 ± 1.9 |

Figure 9:
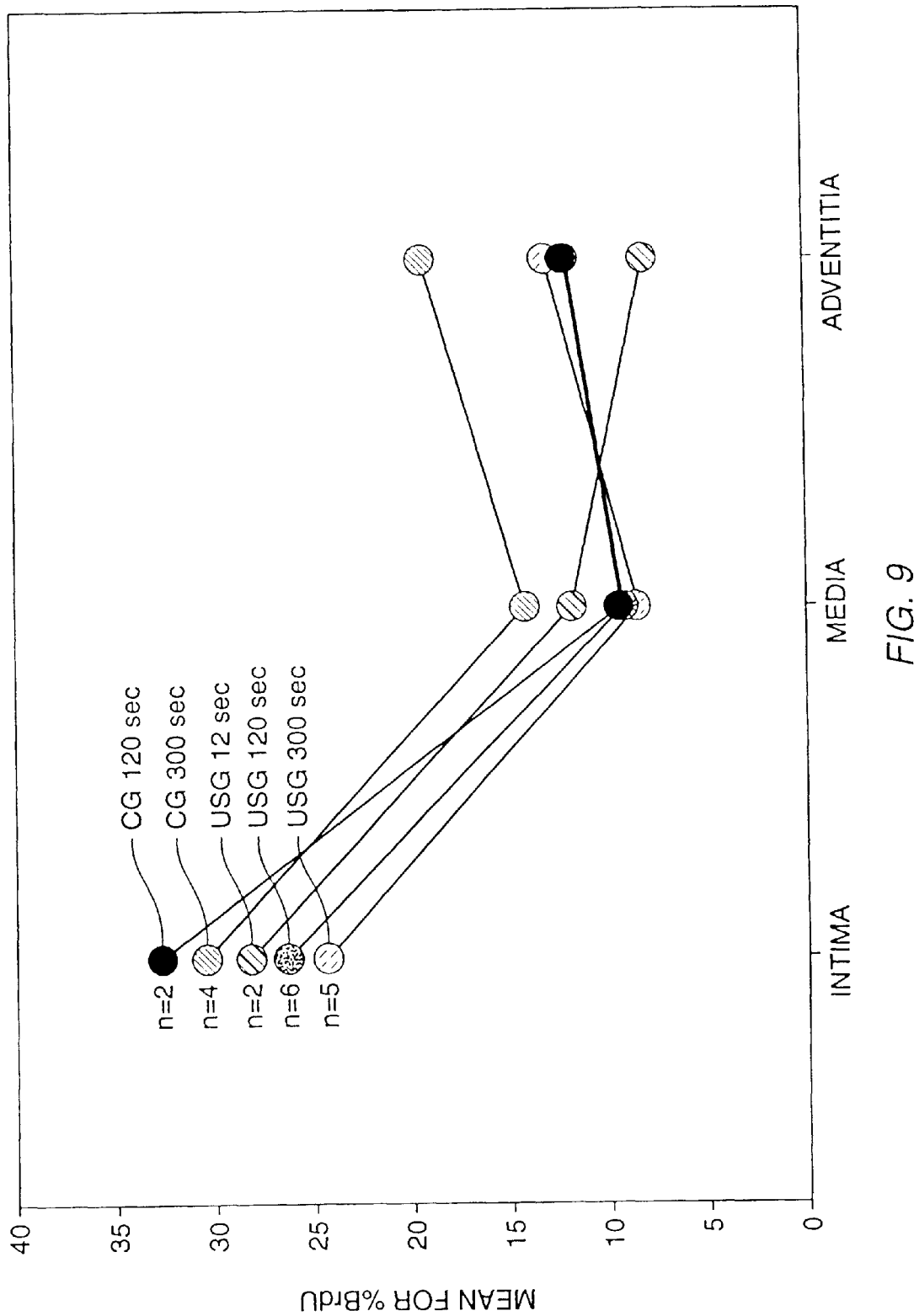
FIG. 9 is a graph showing the differences in smooth muscle cell proliferation in femoral arteries treated with different durations of ultrasonic energy as described in detail in the Experimental section hereinafter.

CG = control group;
USG = ultrasound treated group;
n = number of analyzed segments Cell proliferation study: The mean % BrdU was 32.8±5.4% in the 120-sec CG and 30.4±2.5% in the 300 sec CG. In the US group % BrdU was 28.1±5.5% in the 12-sec group, 26.2±10.6% in the 120-sec group and 24.1±7.0% in the 300-sec group (FIG. 9). 300 sec ultrasound treatment reduced markedly the amount of proliferating smooth muscle cells in the intima (p=0.05 between the control segments and 300 sec treatment segments). The total amount of counted cells and total areas were similar in both groups (Table 3). Acute spasm was noticed twice after sham and once after US treatment. Otherwise there were no acute hemodynamic or electrocardiographic findings associated with either sham treatment or US.

TABLE 3

The effect of balloon and stent injury in sham (CG) and US treated (USG) intima of swine femoral arteries (mean ± SD)

| group | total cell count | total area | % BrdU+ |
|---|---|---|---|
| CG (all) n = 18 | 364.0 ± 110.0 | 0.09 ± 0.02 | 31.2 ± 3.3 |
| USG (all) | 386.5 ± 141.0 | 0.09 ± 0.02 | 25.7 ± 8.2 |
| –12USG (n = 6) | 385.5 ± 285.0 | 0.08 ± 0.02 | 28.1 ± 5.5 |
| –200USG (n = 18) | 348.2 ± 132.7 | 0.09 ± 0.03 | 26.2 ± 10.6 |
| –300USG (n = 15) | 432.8 ± 113.8 | 0.01 to 0.01 | 24.1 ± 0 |

% BrdU = % Bromodeoxyuridine;
SMC = smooth muscle cell;
–12USG = 12 sec ultrasound treatment;
120 USG = 120 sec ultrasound treatment;
300USG = 300 sec ultrasound treatment;
n = number of analyzed segments Intimal hyperplasia studies, stented arteries: These studies conducted at 180 $W/cm^2$ and 120-sec ultrasound exposure time induced an acute spasm twice after sham and twice after US treatment. Otherwise there were no acute hemodynamic or electrocardiographic findings associated with either sham treatment or US. Histological analysis revealed total occlusion in two arteries (one control and one US treated) and deep adventitial dissection also in one US and one sham treated artery. Within the stents, at sites with similar internal elastic lamina disruption (the number of segments n=12 in both groups) US treatment reduced neointimal area 28.9% (CG=4.5±1.2, USG=3.2±1.1 mm2, p<0.05), luminal %stenosis 34.4% (CG=28.5±10.8, USG=18.7±4.7, p<0.01), and mean neointimal thickness 44.2% (CG=247±125 µm., USG=138±84 µm, p<0.05). In spite of a marked b/a ratio, both groups were mainly associated with a mild internal elastic lamina (IEL) rupture (CG 2.0±0.3, USG 2.0±0.3) (Table 4). Only two segments had a severe IEL disruption in both groups. In the US group there was also a tendency for less intramural fibrin/red blood cell content, less chronic inflammation with a same media area (CG 2.0±1.0, USG 1.8±0.6 mm$^2$). In both groups, stented arteries were also re-endothelialized. In the ultrasound treated arteries, based on the visual inspection of the histological slices, there was further a clear reduction in the content of extracellular matrix proteoglycan and total healing of the injury (FIGS. 10A, 10B, 11A, 11B, 12A, 12B, 13A and 13B.) Color prints of these digital photographs are attached in an Appendix to this application.

TABLE 4

The effect of balloon and stent injury on intimal hyperplasia in sham and ultrasound treated swine femoral arteries (n = 12 in both groups), significant of difference * = p < 0.05 (means ± SD)

| parameter | 28CG | 28USG | % reduction |
|---|---|---|---|
| % stenosis | 28.5 ± 10.8* | 18.7 ± 4.7 | 34.4% |
| neointimal thickness | | | |
| over stent struts | 187.7 ± 148.96* | 81.0 ± 61.5 | 56.9% |
| between stent struts | 217.1 ± 148.4* | 95.7 ± 49.7 | 56.8% |
| mean | 247.1 ± 125.0* | 138.0 ± 84 | 44.2% |
| neointimal area | 4.5 ± 1.2* | 3.2 ± 1.1 | 28.9% |
| IEL disruption | 2.0 ± 0.3 | 2.0 ± 0.3 | |
| medial area | 2.1 ± 1.0 | 1.8 ± 0.6 | 10% |
| chronic inflammation | 2.0 ± 0.6 | 1.5 ± 0.9 | 25% |
| fibrin/RBC | 0.7 ± 1.0 | 0.2 ± 0.6 | 72% |

28CG = 28 day control group;
28USG = 28 days US treated group;
IEL = internal elastic lamina;
RBC = red blood cells Intimal hyperplasia study, balloon injured arteries: These studies conducted at 180 W/cm$^2$ and 300-sec ultrasound exposure time induced acute spasm twice after sham treatment and three times after ultrasound treatment. Again no other acute hemodynamic effects were recorded. At 28 days there were no significant differences between the two treatment groups (Table 5). In the ultrasound treated arteries there were slight decreases in chronic inflammation, vessel area, medial area and neointimal area and a minor increase in % stenosis. Sham treated group had on average slightly more IEL disruption, but especially in the sham treated arteries, there was a lot of variability in the initial injury in spite of similar b/a ratio.

TABLE 5

The effect of balloon injury w/o ultrasound treatment on swine femoral arteries at 28 days, n = 9 in both groups (mean ± SD)

| parameter | BG | BUSG | p value |
|---|---|---|---|
| % stenosis | 11.5 ± 19.8 | 16.7 ± 18.6 | ns |
| neointimal area (mm$^2$) | 0.56 ± 1.01 | 0.45 ± 0.57 | ns |
| medical area (mm$^2$) | 1.4 ± 1.2 | 1.1 ± 1.0 | ns |
| EEL (mm$^2$) | 5.4 ± 2.4 | 4.1 ± 1.2 | ns |
| IEL % missing | 13.3 ± 2.5 | 4.3 ± 4.3 | ns |
| chronic inflammation | 0.6 ± 0.9 | 0.8 ± 1.0 | ns |

BG = balloon injured sham group;
BUSG = balloon injured ultrasound group;
EEL = external elastic lamina;
IEL = internal elastic lamina;
p valve = statistical significance;
ns = non-significant While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for inhibiting neointimal hyperplasia in an artery, said method comprising:
    exposing a target site at risk of neointimal hyperplasia within the artery to vibrational energy at a frequency in the range from 100 kHz to 5 MHz, a mechanical index in the range from 0.1 to 50, and a pulse repetition frequency (PRF) in the range from 10 Hz to 10 kHz, in order to inhibit said intimal hyperplasia.

2. A method as in claim 1, wherein the vibrational energy has a frequency in the range from 300 kHz to 3 MHz.

3. A method as in claim 1, wherein the frequency and intensity are selected to produce a mechanical index at the neointimal wall in the range from 0.2 to 10.

4. A method as in claim 3, wherein the vibrational energy is directed against the arterial wall with a pulse repetition frequency (PRF) in the range from 100 Hz to 5 kHz.

5. A method as in claim 4, wherein the energy is directed against the arterial wall with a duty cycle in the range from 0.1 to 100 percent.

6. A method as in claim 5, wherein the energy is directed with a duty cycle in the range from 0.2 to 10%.

7. A method as in claim 1, wherein the elapsed treatment time is in the range from 10 to 900 seconds.

8. A method as in claim 1, wherein the intensity is in the range from 0.01 W/cm$^2$ to 100 W/cm$^2$.

9. A method as in any of claims 1–8, wherein the vibrational energy comprises pressure waves which travel to the arterial wall in substantially radial direction.

10. A method as in any of claims 1–8, wherein exposing the target site comprises:
    positioning an interface surface on or coupled to a vibrational transducer at the target site at a risk of neointimal hyperplasia in the artery; and
    driving the transducer to direct vibrational energy from the interface surface against the arterial wall.

11. A method as in any of claims 1–8, wherein the vibrational energy does not cause significant cavitation in a wall of the artery.

12. A method as in any of claims 1–8, wherein the vibrational energy causes a temperature rise below 10° C. in the wall of the artery.

13. A method as in any of claims 1–8, wherein the vascular smooth muscle cells at least mostly remain viable but in a quiescent state in the neointimal layer after exposure to the vibrational energy.

14. A method as in any of claims 1–8, wherein migration of vascular smooth muscle cells into the neointimal layer is not substantially inhibited.

15. A method as in any of claims 1–8, wherein viability of vascular smooth muscle cells in a medial layer of the artery is not significantly inhibited.

16. A method as in any of claims 1–8, wherein vascular smooth muscle cell proliferation in the neointimal layer exposed to vibrational energy is inhibited by at least 2% after seven days in comparison to such proliferation in a neointimal layer not exposed to the vibrational energy.

17. A method as in any of claims 1–8, wherein the area of the neointimal layer exposed to vibrational energy is inhibited by at least 10% after 28 days in comparison to the area of a neointimal layer not exposed to the vibrational energy.

18. A method as in claim 10, wherein the introducing step comprises:

providing a flexible catheter having at least one ultrasonic transducer disposed near its distal end;

energizing the ultrasonic transducer, wherein the transducer drives the interface surface.

19. A method as in claim 18, wherein the interface surface directly contacts the arterial wall at the target site.

20. A method as in claim 18, wherein the interface surface is spaced-apart from the arterial wall, wherein the ultrasonic energy is transmitted through a liquid medium disposed between the interface surface and the arterial wall.

21. A method as in claim 20, wherein the liquid medium is entrapped within a balloon which is inflated against the arterial wall.

22. A method as in claim 10, wherein the ultrasonically driving step comprises vibrating the surface in a radial direction.

23. A method as in claim 10, wherein the ultrasonically exciting step comprises vibrating the surface in an axial direction.

* * * * *